(12) United States Patent
Gutsche et al.

(10) Patent No.: US 7,943,790 B2
(45) Date of Patent: May 17, 2011

(54) PROCESS FOR PREPARING ALKYLENE OXIDES

(75) Inventors: Bernhard Gutsche, Hilden (DE); Bernd Fabry, Korschenbroich (DE); Stefan Franzen, Kamen (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 12/295,679

(22) PCT Filed: Mar. 23, 2007

(86) PCT No.: PCT/EP2007/002576
§ 371 (c)(1),
(2), (4) Date: Oct. 1, 2008

(87) PCT Pub. No.: WO2007/112866
PCT Pub. Date: Oct. 11, 2007

(65) Prior Publication Data
US 2009/0253944 A1 Oct. 8, 2009

(30) Foreign Application Priority Data

Apr. 1, 2006 (DE) .......................... 10 2006 015 268

(51) Int. Cl.
*C07D 303/00* (2006.01)
*C07D 301/12* (2006.01)
(52) U.S. Cl. ....................................... 549/512; 549/533
(58) Field of Classification Search .................. 549/512, 549/533
See application file for complete search history.

(56) References Cited

U.S. PATENT DOCUMENTS

| 7,678,361 B2 | 3/2010 | Markowz et al. |
| 2002/0028164 A1 | 3/2002 | Schutte et al. |
| 2003/0055293 A1* | 3/2003 | Wurziger et al. ............. 568/451 |
| 2008/0306288 A1 | 12/2008 | Schirrmeister et al. |

FOREIGN PATENT DOCUMENTS

| DE | 10257239 B3 | 7/2004 |
| EP | 0903174 A1 | 3/1999 |
| JP | 2004-285001 A2 | 10/2004 |
| WO | 01/83466 A1 | 11/2001 |
| WO | 2006/020709 A | 2/2006 |
| WO | WO2006020709 * | 2/2006 |
| WO | 2006/042598 A1 | 4/2006 |
| WO | 2004/091771 A | 10/2008 |

OTHER PUBLICATIONS

"Silver-Catalyzed Oxidation of Ethylene to Ethylene Oxide in a Microreaction System" Kestenbaum et al. Ind. Eng. Chem. Res 41, pp. 710-719 (2002).
"Chemie in Mikrostrukturreaktoren" Jahnisch et al. Angewandte Chemie, vol. 116, pp. 410-451 (2004).
"Silicon Micromechanical Devices" Angell et al.: Scientific American vol. 248, No. 4, Apr. 1993, pp. 44-55.
"Development of a Microreactor for Chemical Production" Burns et al.: Trans IChemE, vol. 77 Part A, May 1999 pp. 206-211.
XP002446823, "Mikrostrukturierte Reaktoren fur heterogen katalysierte Gasphasenreaktionen im industriellen Maβstab" Markowz et al.: Chemie Ingenieur Technik, Bd 76, Nr. 5, 2004, pp. 620-625,.
XP008081909, "1-Pentene Epoxidation in Titanium Silicalite-1 Microchannel Reactor. Experiments and Modelling" Chemical Engineering Research and Design, Trans IChemE, vol. 81, Part A, Aug. 2003 pp. 753-759,.
XP-002446824, "Gas-Phase Expoxidation of Propylene and Ethylene Berndt, et al. Ind. Eng. Chem. Res., 2005, 44, pp. 645-650. Chinese Examination Report, Sep. 8, 2010.

* cited by examiner

*Primary Examiner* — Sikarl A Witherspoon

(57) ABSTRACT

The invention provides a process for preparing alkene oxides by contacting in a microreaction system (µ-reactor) a $C_2$-$C_3$ alkene with an oxidizing agent comprising a peroxo compound.

17 Claims, No Drawings

PROCESS FOR PREPARING ALKYLENE OXIDES

CROSS REFERENCE TO RELATED APPLICATIONS

This application is the National Phase entry of PCT/EP2007/002576, filed Mar. 23, 2007, which claims priority to German patent application number DE 10 2006 015 268.9 filed Apr. 1, 2006, both of which are incorporated herein by reference in their entireties.

FIELD OF THE INVENTION

The invention is in the field of petrochemistry and relates to an improved process for preparing ethylene oxide or propylene oxide using structured microreactors.

BACKGROUND OF THE INVENTION

Alkylene oxides, such as ethylene oxide and propylene oxide, are some of the most important mineral oil-based industrial chemicals. Ethylene oxide (EO) in particular is a starting material for the preparation of ethylene glycol, which is added, for example, to aviation gasoline as an antifreeze. Since ethylene oxide and propylene oxide are additionally also depleted by a reaction with all kinds of substances which possess acidic hydrogen atoms, they are suitable, for example, for addition onto alcohols or amines to form polyalkylene glycol chains which impart a hydrophilic character to these substances. The significant outlet for this type of compounds is that of nonionic surfactants, which find use especially in washing compositions and cosmetics. The reaction of ethylene oxide or propylene oxide with ammonia affords alkanolamides; with carbon dioxide, ethylene carbonate and propylene carbonate are obtained, which are likewise intermediates of interest for industrial chemistry.

Ethylene oxide and propylene oxide are now prepared nearly exclusively by direct oxidation of the corresponding alkylenes over silver catalysts:

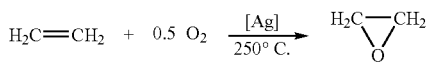

The reaction is, for example, exothermic by 120 kJ/mol for ethylene oxide and competes with the complete combustion of the ethylene to carbon dioxide, which proceeds significantly more exothermically at more than 1300 kJ/mol. Ethylene oxide is prepared industrially, for example, generally in tube bundle reactors which may contain up to 1000 individual tubes and are cooled from the outside with a liquid heat carrier, for example tetralin, in order also to be able to maintain the oxidation temperature of from 230 to 270° C. even in the case of increasing total oxidation. The catalyst, for example 15% by weight of silver on $Al_2O_3$, is present as a bed in the tube. In general, preference is given to oxidation with oxygen. Nevertheless, the conversion of ethylene is limited to about 10 to 15%, since only in this way can selectivities of not more than 75 to 80% be achieved. About one quarter of the expensive starting material is thus combusted to carbon dioxide in this way. An additional factor is that typically up to 2.5% by volume of water and up to 10% by volume of carbon dioxide are present in the end product, which have to be removed before the further utilization with a high level of technical complexity. The problems in the preparation of propylene oxide are comparable.

An article by Schüth et al. in Ind. Eng. Chem. Res 41, 701-719 (2002) discloses the use of microreactors for silver-catalyzed oxidation of ethylene to ethylene oxide. The oxidizing agent used here is pure oxygen. German patent DE 10257239 B3 (ACA) discloses a process in which olefins, for example including ethylene, are oxidized in the presence of a photosensitizer, the reaction being effected in a multitude of micro-falling-film reactors running parallel to one another. The oxidizing agent used here too is oxygen. International patent application WO 01/083466 A1 (Merck) proposes a process for epoxidation of functionalized olefins, in which the reaction is likewise effected in microreactors, but under mild conditions in the liquid phase. The reaction is additionally performed without catalysts. A similar process for preparing active pharmaceutical ingredients is known from Japanese patent application JP 2004-285001 A2 (Sumitomo): here, it is proposed to react on saturated feedstocks, for example methyl 3-dimethyl-2-(2-methyl-1-propenyl) cyclopropanecarboxylate, with ozone in the liquid phase, and the reaction can take place in a microreactor; but the oxidation of ethylene or propylene is not mentioned here.

It was therefore an object of the present invention to provide a process for industrially preparing ethylene oxide or propylene oxide, which is free of the disadvantages of the prior art and, especially at high conversions, affords improved selectivities and space-time yields, and suppresses the undesired total oxidation of the feedstocks as far as possible.

DETAILED DESCRIPTION OF PREFERRED EMBODIMENTS

The invention provides a process for preparing ethylene oxide and/or propylene oxide by contacting ethylene and/or propylene with an oxidizing agent, wherein
(i) the reaction takes place in a microreaction system (μ-reactor) and
(ii) the oxidizing agent used is a peroxo compound.

It has been found that, surprisingly, both the reaction of ethylene and propylene and mixtures of the two gases with oxidizing agents, for example ozone or hydrogen peroxide, can be carried out irrespective of the explosion limits. Especially when ozone is used, it is possible to work with the technically possible maximum concentrations. The process according to the invention not only improves the selectivity and the space-time yield, which makes the preparation of the target products significantly more economic, but total oxidation is also simultaneously substantially prevented. This leads not only to a saving of raw materials, but the reaction end product is additionally also virtually free of by-products, such that the otherwise obligatory and technically complicated drying and $CO_2$ removal can be dispensed with. At the same time, the process allows operation of an oxygen cycle. Finally, a further advantage is that the reaction can be performed without catalysts.

Structured Reactors and Microreaction Systems

A central element of the present invention consists in the finding that structured reactors enable the oxidation of ethylene and propylene to be performed irrespective of the explosion limits, since the reaction can be conducted isothermally, the reactants have only a minimal residence time in the reactor and the reaction channels have diameters which do not exceed the maximum experimental safe gap. The term "maximum experimental safe gap" is understood to mean the maximum diameter of a reactor at which a flame resulting from explosion is still automatically extinguished. These circumstances make it possible to use any mixtures of ethylene or propylene and oxidizing agent and nevertheless also to operate the reactor safely in the explosion range.

The term "structured reactor" is understood to mean an array of reaction channels which can be operated individually, in modules or else altogether and are disposed in a matrix which serves for stabilization, securing, heating or cooling. A preferred embodiment of a structured reactor is that of microreaction systems, which are also referred to in general as micro- or µ-reactors. They have the feature that at least one of the three dimensions of the reaction chamber has a measurement in the range from 1 to 2000 µm, and they thus feature a high transfer-specific inner surface area, short residence times of the reactants and high specific heat and mass transfer performances. A detailed article on this subject can be found, for example, in Jähnisch et al. in Angewandte Chemie Vol. 116, 410-451 (2004). Reference is made by way of example to European patent application EP 0903174 A1 (Bayer), in which the liquid phase oxidation of organic compounds in a microreactor consisting of an array of parallel reaction channels is described. Microreactors may additionally comprise microelectronic components as integral constituents. In contrast to known microanalytical systems, it is by no means necessary in the microreactors that all lateral dimensions of the reaction chamber are within the µm range. Instead, their dimensions are determined exclusively by the type of reaction. Accordingly, for particular reactions, useful microreactors are also those in which a particular number of microchannels is bundled, such that micro- and macrochannels or parallel operation of a multitude of microchannels may be present alongside one another. The channels are preferably arranged parallel to one another in order to enable a high throughput and to keep the pressure drop as low as possible.

Support

The supports in which the structure and dimensions of the microreaction systems are defined may be material combinations, for example silicon-silicon, glass-glass, metal-metal, metal-plastic, plastic-plastic or ceramic-ceramic, or combinations of these materials, although the preferred embodiment is a silicon-glass composite. Useful supports also include polyacrylates which are produced by layer-by-layer hardening and are particularly inexpensive to produce. A further alternative is that of HAT ceramics, specifically those which are surrounded by a pressure-resistant jacket, and also all-metal reactors in which the reaction channels are coated appropriately to prevent decomposition of the oxidizing agent. A wafer of thickness, for example, from 100 to 2000 µm, preferably about 400 µm, is structured preferably by means of suitable microstructuring or etching techniques, for example reactive ion etching, through which it is possible, for example, to manufacture three-dimensional structures irrespective of the crystal orientation in silicon [cf. James et al. in Sci. Am. 4, 248 (1993)]. It is also possible, for example, to treat microreactors of glass in the same way.

Wafers treated in this way may have from 10 to 1000, preferably from 100 to 500 and especially from 200 to 300 microreaction systems running parallel to one another, which may be actuated and operated either in parallel or sequentially. The geometry, i.e. the two-dimensional profile of the channels, may be very different: possible profiles include straight lines, curves, angles and the like, and combinations of these shape elements. Not all microreaction systems need have the same geometry. The structures feature measurements of from 50 to 1500 µm, preferably from 10 to 1000 µm, and vertical walls, the depth of the channels being from 20 to 1800 µm and preferably from about 200 to 500 µm. The cross sections of each microreaction chamber, which may but need not be square, are generally in the order of magnitude of from 20×20 to 1500×1500 µm$^2$ and especially from 100×100 to 300×300 µm$^2$, as is specified as typical, for example, by Burns et al. in Trans IChemE 77(5), 206 (1999). To supply the microreaction chambers with the reactants, the wafer is etched through at the points intended for this purpose.

Finally, the structured wafer is bonded by a suitable process, for example anodic bonding, to a further wafer, for example of glass, preferably Pyrex glass, and the individual flow channels are sealed tightly to one another. Of course, depending on the substrate material, other construction and bonding techniques are also possible to realize impervious flow systems, which will be apparent to the person skilled in the art, without any need for an inventive step for this purpose.

Structuring of the Microreactors

The microreaction systems may be divided into one or more mixing zones, one or more reaction zones, one or more mixing and reaction zones, one or more heating and cooling zones, or any combinations thereof. They preferably have three zones, specifically two reaction zones and one cooling zone, as a result of which especially two- or multistage reactions can be carried out efficiently in the liquid phase or else in the gaseous phase. In the first zone, two reaction participants are mixed and reacted; in the second zone, the reaction between the product of the first zone and a further reactant takes place, while the termination of the reaction is brought about in the third zone by lowering the temperature. It is not absolutely necessary to thermally strictly separate the first reaction zone and the second reaction zone from one another. Specifically, when the addition of a further reactant is required or several mixing points are desired instead of one, this can also take place in reaction zone 2 over and above zone 1. The microreaction systems may be operated sequentially or else simultaneously, i.e. in parallel with defined amounts of reactant in each case and have identical or different geometries. A further possible way in which the geometry of the microreaction systems may differ consists in the mixing angle at which the reactants meet one another and which may be between 15 and 270° and preferably from 45 to 180°. Furthermore, it is possible to cool or to heat each of the three zones independently, or to vary the temperature within one zone as desired, the reaction chambers in this example being channels whose length per zone may be from 10 to 500 mm.

Oxidation of Alkylenes

The oxidizing agents used to prepare ethylene oxide or propylene oxide from the corresponding alkenes in the context of the present invention are peroxo compounds, for example ozone, hydrogen peroxide or performic acid. Particular preference is given to the use of mixtures of hydrogen peroxide and ozone. In addition, the two reactants can be used in a stoichiometric molar ratio. As a free-radical former, it is advisable to add, for example, $NO_2$. However, a particular advantage of the process, by virtue of an isothermal method and short residence times, is the use of any mixtures of ethylene or propylene and oxidizing agent. Even in the theoretical case of an explosion, the flames would additionally self-extinguish, since the dimensions of the microreaction systems are below the maximum experimental safe gap. When the oxidizing agent used is ozone, preference is given to working at the technically achievable maximum ozone concentration, i.e. up to 196 g/m$^{-3}$ (STP), i.e. 12-13% by weight when pure oxygen is used, or 60 g/m$^{-3}$ (STP) or 4-5% by weight when atmospheric oxygen is used.

It is also possible to add inert gases, for example methane, in amounts up to 50% by volume; when air is used, this becomes unnecessary as a result of the presence of nitrogen. The reaction temperature may be between 100 and 300° C. The oxidation proceeds preferably at from 180 to 250° C. and especially from 190 to 220° C. When a gaseous oxidizing agent is used, it can be added directly to the ethylene or propylene; when, for example, hydrogen peroxide is used, it is advisable to feed the reactants separately into the microreaction system and to mix them in a mixing zone. The reaction can be effected in the range from 0.1 to 1 mbar, preferably from 10 to 100 mbar. Higher pressures generally lead to lower selectivity in the direction of the target products.

Workup of the Reaction Mixture

After leaving the microreaction system, the individual product streams are combined. As already explained at the outset, a particular advantage of the process is that total oxidation is substantially suppressed and a further workup is not required for many applications owing to the low water and carbon dioxide contents.

In the case that the alkylene oxide should be substantially free of water and $CO_2$, the workup can be effected in a manner known per se: to this end, the alkylene oxide is first scrubbed out with water in an absorber, before it is then distilled out of the aqueous solution in a stripper. Ethylene or propylene is added again to the unconverted residual gas up to the desired concentration. Subsequently, it is compressed to from 5 to 25 bar, the carbon dioxide present is extracted with a scrubbing solution and the desired concentration of the oxidizing agent is established. Subsequently, the gas mixture is recycled back into the microreaction systems.

EXAMPLES

Examples 1 to 5

For the experiments, a microreaction system consisting of a 400 μm-thick silicon wafer was used, which was joined to a Pyrex glass wafer. 20 parallel, linear channels, with a depth of 300 μm and a cross section of the microreaction chambers of 300×300 μm² had been etched into the silicon wafer. The channels were operated in parallel and were each etched through for reactant introduction and for product removal. The formation of ethylene oxide or propylene oxide by the action of ozone or hydrogen peroxide, optionally in the presence of small amounts of $NO_2$ as a free-radical former, on ethylene or propylene was studied. The results are compiled in table 1 (mean value from five measurements).

TABLE 1

| Experimental results | | | | | |
|---|---|---|---|---|---|
| Parameter | 1 | 2 | 3 | 4 | 5 |
| c(ethylene) [% by vol.] | 5 | 10 | 5 | — | — |
| c(propylene) {% by vol.] | — | — | — | 5 | 10 |
| Oxidizing agent | $O_3$ | $O_3$ | $H_2O_2$ | $O_3$ | $O_3$ |
| c(oxidizing agent) [% by vol.] | 95 | 90 | 95 | 95 | 90 |
| Temperature [° C.] | 275 | 275 | 275 | 275 | 275 |
| Pressure [mbar] | 100 | 100 | 100 | 100 | 100 |
| Residence time [s] | 0.2 | 0.2 | 0.2 | 0.2 | 0.2 |
| Ethylene conversion [%] | 10 | 8 | 9 | 20 | 18 |
| Selectivity for EO/PO [%] | 95 | 92 | 94 | 93 | 91 |
| Selectivity for $CO_2$ [%] | <0.1 | <0.1 | <0.1 | <0.1 | <0.1 |

As the examples show, significantly higher selectivities are achieved in accordance with the process according to the invention than had been possible to date according to the prior art. More particularly, total oxidation is also virtually completely suppressed.

The invention claimed is:

1. A process for preparing alkylene oxides, comprising reacting, in a microreaction system (μ-reactor), an alkene with an oxidizing agent in the absence of a catalyst, wherein said oxidizing agent is ozone.

2. The process of claim 1, wherein the microreaction system is mounted on a support.

3. The process of claim 1, wherein the microreaction system has at least one inlet for the reactants and at least one outlet for the products.

4. The process of claim 2, wherein the support is a silicon-glass composite.

5. The process of claim 2, wherein the microreaction systems are applied to the support by microstructuring techniques.

6. The process of claim 2, wherein the support has from about 10 to about 1000 microreaction systems which run parallel to one another and can be sequentially actuated with the reactants.

7. The process of claim 6, wherein the microreaction systems all have the same geometry.

8. The process of claim 7, wherein the microreaction systems have dimensions in the range from about 50 to about 1500 μm in at least one dimension.

9. The process of claim 8, wherein the microreaction systems have a depth of from about 20 to about 1800 μm.

10. The process of claim 9, wherein the microreaction systems have cross sections of from about 20×20 to about 1500×1500 μm².

11. The process of claim 10, wherein the microreaction systems are channels which have a length of from about 1 to about 500 μm.

12. The process of claim 11, wherein the microreaction systems have one or more mixing zones, one or more reaction zones, one or more mixing and reaction zones, one or more heating or cooling zones, or any combination thereof.

13. The process of claim 1, wherein at least a portion of said reaction is performed at a temperature of from about 100 to about 300° C.

14. The process of claim 1, wherein at least a portion of the reaction is performed at a pressure of from about 0.1 to about 1 bar.

15. The process of claim 2, wherein the support has from about 10 to about 1000 microreaction systems which run substantially parallel to one another and can be substantially simultaneously actuated with the reactants.

16. The process of claim 15, wherein each microreaction system has a different geometry.

17. The process of claim 1 wherein said alkene comprises ethylene, propylene, or mixtures thereof.

* * * * *